United States Patent [19]

Lamphere et al.

[11] 4,062,223
[45] Dec. 13, 1977

[54] NITROGEN CONTENT MONITOR FOR LIQUIFIED NATURAL GAS

[75] Inventors: David A. Lamphere, Milton; Paul G. Weitz, Jr., Salisbury, both of Vt.

[73] Assignee: Simmonds Precision Products, Inc., Tarrytown, N.Y.

[21] Appl. No.: 721,897

[22] Filed: Sept. 9, 1976

[51] Int. Cl.² ............................................. G01N 25/18
[52] U.S. Cl. ...................................... 73/27 R; 62/49; 73/61.1 R
[58] Field of Search ................... 73/27 R, 32 R, 17 A, 73/61.1 R, 61.3; 62/49, 125; 324/65 R

[56] References Cited

U.S. PATENT DOCUMENTS

| | | | |
|---|---|---|---|
| 2,594,683 | 4/1952 | Rolfson | 73/17 A |
| 3,383,881 | 5/1968 | Bailey | 62/49 |
| 3,695,095 | 10/1972 | Lineburg | 73/61.3 |
| 3,926,038 | 12/1975 | Wunning et al. | 73/61.1 R |
| 3,964,037 | 6/1976 | Lamphere | 73/32 R |

OTHER PUBLICATIONS

Rovinskii, "A Liquid Helium Level Indicator", Cryogenics, p. 115, 12-1961.

Primary Examiner—Richard C. Queisser
Assistant Examiner—Stephen A. Kreitman
Attorney, Agent, or Firm—Edwin E. Greigg

[57] ABSTRACT

A monitoring system for determining the volumetric percentage of liquid nitrogen in a quantity of liquified natural gas (LNG) whose composition of liquified hydrocarbon gases is known, and which is stored at atmospheric pressure. The system includes a device, such as a temperature-dependent resistor connected to a power source, for producing an electric signal proportional to the temperature of the liquified gas. This temperature signal is subtracted from a reference signal which is equal to the temperature signal when the liquified natural gas does not contain any nitrogen, and which can be produced by a device such as a precision resistor connected to the power source. The differential signal output of the temperature and reference signals will be proportional to the volumetric percentage of nitrogen in the liquified natural gas, and a standard readout device, such as a voltmeter, can be calibrated to read the volumetric percentage of nitrogen from this differential signal.

8 Claims, 3 Drawing Figures

NITROGEN CONTENT MONITOR FOR LIQUIFIED NATURAL GAS

BACKGROUND OF THE INVENTION

1. Field of the Invention

The invention relates generally to volumetric analysis of a component of a cryogenic liquid, in particular, to a system for determining the percent by volume of liquid nitrogen in a stored quantity of liquified natural gas (LNG) whose composition of liquified hydrocarbon gases is known, and which is stored at atmospheric pressure.

2. Description of the Prior Art

At the present time, the only method which is used to determine the amount of nitrogen present in a quantity of liquified natural gas is that of taking a sample and analyzing it for all of the liquid components. This procedure is time consuming and subject to error, especially since the nitrogen present in the liquified natural gas normally constitutes only a small percentage of the total quantity of the liquid.

It is desirable to know the nitrogen content of stored liquified natural gas because such nitrogen is an inert component of the liquid, with no heating value; consequently, any nitrogen present has a deleterious effect on the heating value of the liquid, upon which the monetary value of the liquified natural gas is based. Also, continuous monitoring of the LNG nitrogen content is desirable, since nitrogen is more volatile than the LNG hydrocarbon components, and will boil off during storage. In addition, the measured nitrogen content can be used with LNG density measuring equipment to correct for minor density-dielectric constant variations in a LNG mixture.

OBJECTS AND SUMMARY OF THE INVENTION

Accordingly, a primary object of this invention is to disclose a nitrogen content monitoring system which can be used to determine and continuously monitor the nitrogen content of a quantity of stored liquified natural gas of a known composition of liquified hydrocarbon gases, in which the only measurement required is the temperature of the liquified natural gas.

For any particular composition of liquified natural gas at normal atmospheric pressure, the boiling temperature will vary in dependence on the nitrogen content of the composition. Since liquified natural gas is always store in bulk at atmospheric pressure because of tank structural considerations, if the composition of the major LNG components are known, that is, the type and relative quantities of the liquified hydrocarbon gaseous components, the quantity of nitrogen present in the mixture can be determined solely from the temperature of the boiling liquid. Thus, for continuous monitoring of the LNG nitrogen content, all that is required is a temperature measuring device immersed in the boiling liquid which produces an electrical signal proportional to the boiling temperature, and an indicating instrument for measuring this temperature signal which is calibrated for the particular LNG composition to read directly in percent by volume of the LNG nitrogen content. An amplifier may be deposed between the temperature sensor and the indicating instrument. Also, the temperature singal may be conditioned by subtracting from it a reference signal which is equal to the temperature signal produced for the particular LNG composition when there is no nitrogen present to thereby allow full scale deflection of the indicating instrument over the anticipated range of nitrogen content. Either an analog or digital readout instrument may be used. Where the temperature signal is not a straight line function of the nitrogen content, a non-linear network of resistors and semiconducting devices (diodes, transistors, thyristors) can be used intermediate to the temperature sensor and the readout device to produce a temperature signal directly proportional to the nitrogen content.

Another object of the invention is to disclose a nitrogen content monitoring system as described above, which can be easily recalibrated for use with different compositions of stored LNG. If the current or voltage across a reference resistor is used as the zero nitrogen content reference signal, all that is necessary to change the reference signal required for a different LNG mixture is to use a different reference resistor, or adjust a variable reference resistor. Similarly, the rate of change of the temperature signal with temperature can be adjusted by the use of different, series connected, signal voltage or current dropping resistors, or by the use of different non-linear networks, for different LNG compositions. All of these signal conditioning resistive elements or circuits for a particular LNG composition can be grouped together on a plug-in board or module, to thus simplify the recalibration required when the system is used to monitor a different LNG mixture. Alternately, several variable resistors can be adjusted each time a different LNG composition is monitored.

The invention will be better understood as well as other objects and advantages thereof become more apparent from the following detailed description of the invention taken in conjunction with the drawing.

DESCRIPTION OF THE PREFERRED EMBODIMENTS

Figure 1:
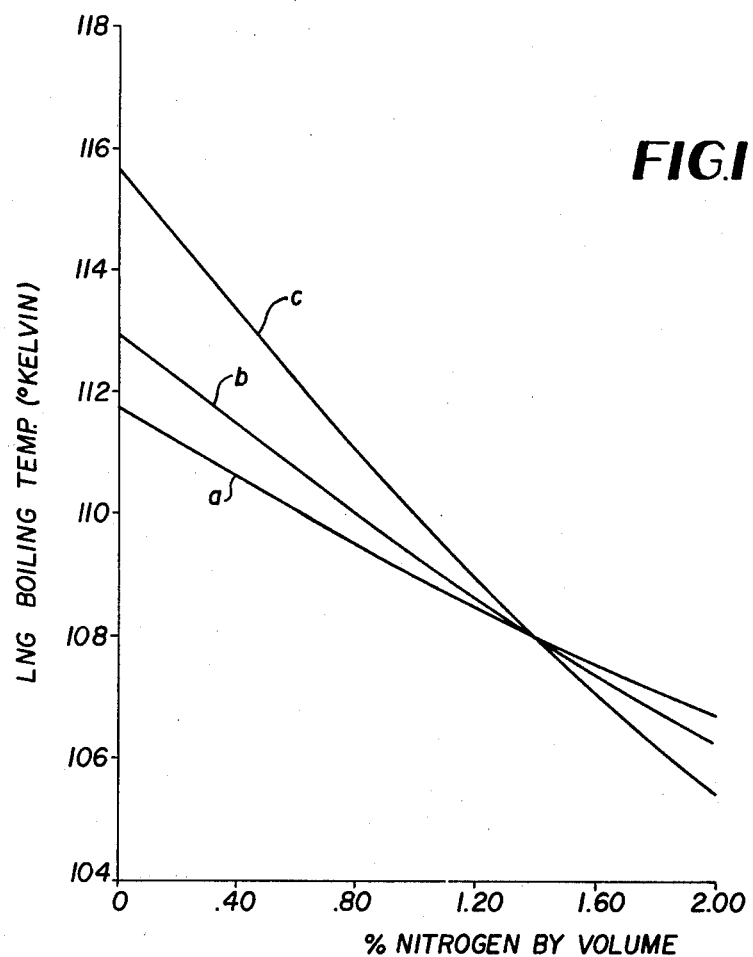
FIG. 1 is a graphical representation of the variation of liquid boiling temperature with the nitrogen content of representative LNG mixtures at normal atmospheric pressure.

In FIG. 1, the variation of LNG boiling temperature at normal atmospheric pressure with the percent by volume of the LNG nitrogen content is shown for three representative LNG mixtures: Curve $a$ applies to a LNG mixture in which 100% of the liquified hydrocarbon gas portion is $CH_4$; Curve $b$ applies to a LNG mixture in which 90% of the liquified hydrocarbon gas portion is $CH_4$, and the remaining 10% is $C_2H_6$; and Curve $c$ applies to a LNG mixture in which 70% of the liquified hydrocarbon is $CH_4$, and the remaining 30% is $C_2H_6$. Similar relationships of LNG boiling temperature and nitrogen content exist for other LNG mixtures. Also, these curves can be corrected for variations from normal atmospheric pressure, to be used, for example, when a LNG mixture is stored at a high altitude location.

From the representative curves shown in FIG. 1, it is readily seen that the LNG nitrogen content can be determined solely from the liquid temperature. For example, referring to Curve a, the boiling temperature at standard atmospheric pressure of liquified $CH_4$ is about 111.7° Kelvin, but in a LNG mixture of $CH_4$ and nitrogen, when the nitrogen content of the mixture is 1.4% by volume, the boiling temperature is only about 180° Kelvin. Normally, the nitrogen content is a very small percentage of the total LNG volume, which, as can be seen from FIG. 1, varies substantially as a straight-line function of the LNG boiling temperature. Thus, only two variable resistors can be utilized to recalibrate this monitoring system for use with different LNG mixtures: a reference resistor to adjust the zero nitrogen content reference signal, and a voltage divider to match the readout device with the slope of the liquid temperature-nitrogen line.

Using a family of curves, such as those of FIG. 1, the temperature and content values of an intermediate mixture can be interpolated. Thus, if the LNG mixture is unknown, a complete volumetric analysis can be performed only once, the correct temperature-nitrogen content relationship determined and the system calibrated for that relationship. Thereafter, the nitrogen content of the LNG mixture can be continuously monitored.

Figure 2:
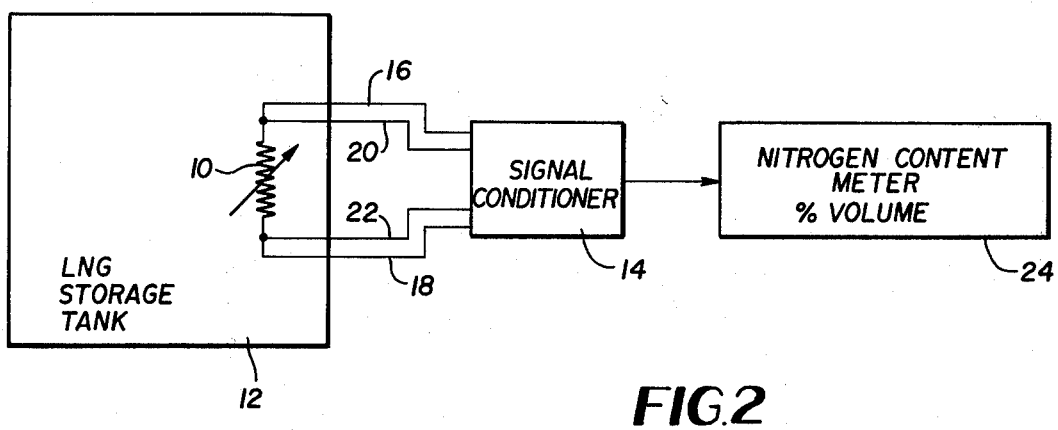
FIG. 2 is a block diagram of an embodiment of the invention in which a temperature-dependent resistance element is used to sense the LNG temperature.

In FIG. 2, a temperature-dependent resistor 10, which is immersed in a LNG mixture within a LNG storage tank 12, is connected to an electric power source within a signal conditioner 14 by the lines 16, 18. The voltage drop across the resistor 10, which is proportional to the LNG temperature, is used as a temperature signal and is transmitted to the signal conditioner 14 by the lines 20, 22. The signal conditioner 14 includes known circuitry for producing a proper input signal to a readout device 24. For example, a standard resistance balance bridge circuit can be connected across the power supply, with the sensor resistor 10 and a reference resistor connected in opposite legs so that the output signal is zero when there is no nitrogen present in the LNG mixture. Alternately, a circuit similar to the circuit disclosed in U.S. Pat. No. 3,903,478, issued Sept. 2, 1975, for a fluid density measuring device, can be used to subtract a reference signal from the temperature signal, using resistors as the sensor and reference elements, rather than the capacitive sensor and reference elements used in U.S. Pat. No. 3,903,478.

The readout device 24 can be a standard analog or digital voltmeter, and can be either an indicating or recording instrument.

The signal condition 14 can include a voltage divider circuit for the output signal, which can be made adjustable so that the system can be easily recalibrated for use with different LNG mixtures. Alternately, these resistance calibrating elements can be fixed resistors, but mounted in a plug-in module, so that different modules, each corresponding to a particular LNG mixture, can be used. Similarly, if a non-linear resistive semiconductor network circuit is included in the signal conditioner 14 to produce a voltage signal to the readout device 24 which is directly proportional to the LNG nitrogen content, elements of the non-linear network can also be included in a plug-in module of the signal conditioner 14.

Figure 3:
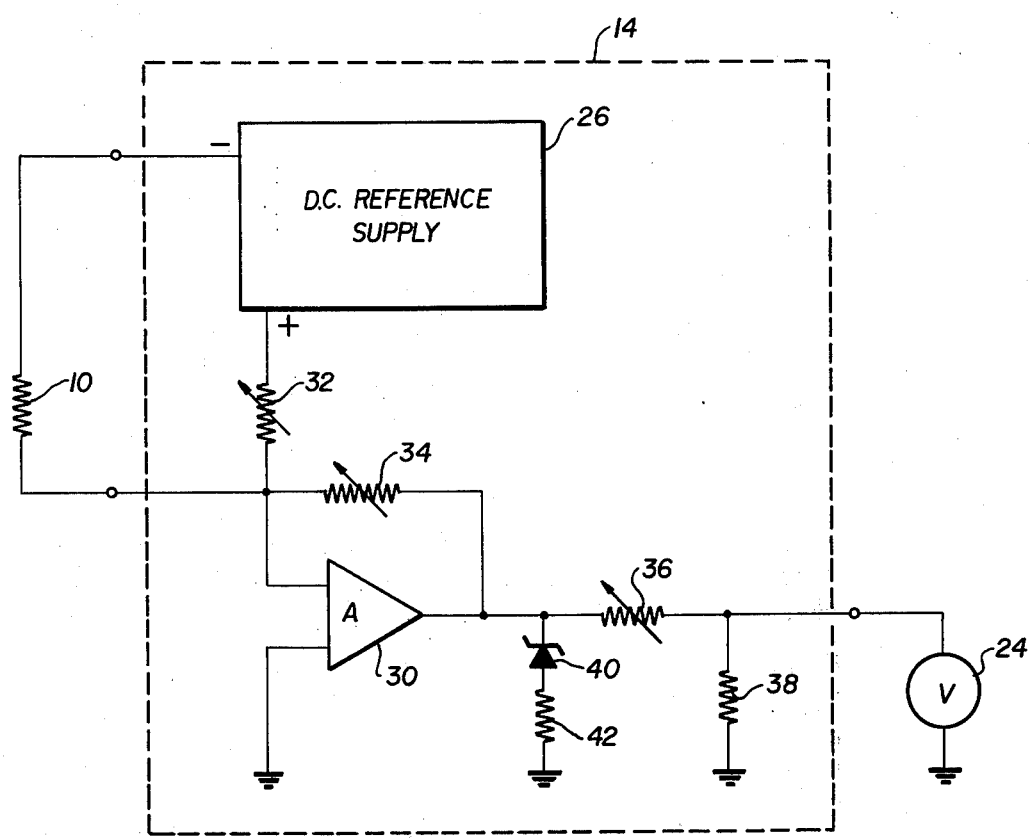
FIG. 3 is a block diagram of a signal conditioner circuit of this invention.

FIG. 3 is a block diagram of a simple embodiment of the signal conditioner 14, in which the calibrating resistors and circuits discussed above are shown. The signal conditioner 14 includes a D.C. reference supply 26 and an amplifier 30. One input of the amplifier 30 is connected through the temperature-dependent resistor 10 to one polarity of the reference supply 26, and through the zero content reference resistor 32 to the opposite polarity of the reference supply 26. The other input of the amplifier 30 is connected to ground. Thus, when there is no nitrogen present in the LNG mixture, the resistance of the temperature-dependent resistor 10 will be equal to the resistance of the reference 32, and there will be no input signal to the amplifier, since the signal from the resistor 10 will be equal and opposite to the signal from the reference resistor 32. When nitrogen is present in the LNG mixture, the resistance of the temperature-dependent resistor 10 will be less than that of the reference resistor 32, and the input signal to the amplifier 30 will be the difference of the two signals from the reference supply 26. The output signal of the amplifier 30 can be adjusted by a variable resistor 34 in its feedback circuit, or by a variable resistor 36, which with another resistor 38 connected to ground, constitutes a voltage divider circuit with the nitrogen content meter 24 being connected between the common side of the resistors 36, 38 to ground. Also, one or more non-linear elements, such as the zener diode 40 connected in series with the resistor 42 to ground can be connected in parallel with the resistors 36, 38 to form a non-linear network, so that the voltage signal to the meter 24 is directly proportional to the nitrogen content.

What is claimed is:

1. A nitrogen content monitoring system for determining the nitrogen content of stored liquified natural gas (LNG) having a known composition of liquified hydrocarbon gases and stored at atmospheric pressure, which comprises, in combination:

temperature measurement means for producing a first electrical signal proportional to the temperature of the liquified natural gas;

signal conditioning means for conditioning said first electrical signal to produce a second conditioned signal proportional to the nitrogen content of the liquified natural gas, said signal conditioning means including: means for producing a third reference signal which is equal to said first signal when the liquified natural gas contains no nitrogen; and means for subtracting said third reference signal from said first signal to produce said second conditioned signal; and readout means for indicating the nitrogen content of the liquified natural gas from said second conditioned signal.

2. A nitrogen content monitoring system, as described in claim 1, wherein the temperature measurement means includes:

an electrical power supply; and a temperature-dependent resistor, disposed in the liquid natural gas and connected to said power supply.

3. A nitrogen content monitoring system, as described in claim 1, wherein the signal conditioning means further includes amplifier means for amplifying the difference between the third reference signal and the first signal to produce said second conditional signal.

4. A nitrogen content monitoring system, as described in claim 1, wherein said means for producing a third reference signal includes:

a reference resistor connected to said power supply.

5. A nitrogen content monitoring system, as described in claim 4, wherein said reference resistor is a variable resistor.

6. A nitrogen content monitoring system, as described in claim 1, wherein the signal conditioning means further comprises a non-linear network having a voltage output which is directly proportional to the percentage of nitrogen present in the liquified natural gas, whereby said voltage output comprises said second conditioned signal.

7. A nitrogen content monitoring system, as described in claim 1, wherein said readout means includes a voltmeter.

8. A nitrogen content monitoring system, as described in claim 7, wherein said voltmeter is a digital voltmeter.

* * * * *